US00PP11090P

United States Patent [19]

Zaiger et al.

[11] Patent Number: Plant 11,090

[45] Date of Patent: Oct. 12, 1999

[54] PEACH TREE 'COUNTRY SWEET'

[76] Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, Calif. 95358

[21] Appl. No.: 09/009,780

[22] Filed: Jan. 20, 1998

[51] Int. Cl.[6] ..... A01H 5/00

[52] U.S. Cl. ..... Plt./197

[58] Field of Search ..... Plt./197

[56] References Cited

U.S. PATENT DOCUMENTS

P.P. 1,716 7/1958 Vestal ..... Plt./197

P.P. 5,474 5/1985 Zaiger ..... Plt./197

*Primary Examiner*—Howard J. Locker

*Assistant Examiner*—Wendy A Baker

[57] ABSTRACT

The present new and distinct variety of peach tree (*Prunus persica*) has the following unique combination of features that are desirable in a new variety. The following features of the tree and its fruit are characterized with the tree budded on nemaguard rootstock, grown on Hanford sandy loam soil with Storie Index rating 95, in USDA Hardiness Zone 9, near Modesto, Calif., and with standard commercial cultural fruit growing practices, such as, pruning, thinning, spraying, irrigation, fertilization:

1. Heavy and regular production of large size fruit.
2. Fruit with a mild, sweet, sub-acid flavor and excellent eating quality.
3. Fruit with firm, yellow flesh, good storage and shipping quality.
4. Fruit that will hold firm on the tree 10 to 12 days after maturity (shipping ripe).
5. Fruit with a high degree of attractive red skin blush.
6. Vigorous, upright growth.

1 Drawing Sheet

ORIGIN OF THE VARIETY

The present new and distinct variety of peach tree was originated by us in our experimental orchard located near Modesto, Calif., as a first generation cross between two selected seedlings with field identification numbers 36EB86 and 9GC175. The peach seedling 36EB86 (non-patented) which is the material parent, was selected as an addition to our gene pool to be used in our fruit breeding program, originated from a second generation seedling that was selected from a cross between May Grand Nectarine (U.S. Plant Pat. No. 2,794) and a peach of unknown parentage. The paternal parent 9GC175 (non-patented), was also selected for use in our fruit breeding program, it originated from a second generation seedling of a cross between an open pollinated seedling of Early Sun Grand Nectarine (U.S. Plant Pat. No. 1,420) and Royal Gold Peach (U.S. Plant Pat. No. 2,663). A large group of these first generation seedlings, growing on their own root, were planted and maintained under close observation, during which time we recognized the desirable fruit characteristics described above and selected the present variety for asexual reproduction and commercialization.

ASEXUAL REPRODUCTION OF THE VARIETY

Asexual reproduction of the new and distinct variety of peach tree was by budding to Nemaguard rootstock, the standard rootstock for peaches and nectarines in California, as performed by us in our experimental orchard located near Modesto, Calif., and shows that all characteristics of the tree and its fruit run true to the original tree and are established and transmitted through succeeding asexual propagations.

SUMMARY OF THE VARIETY

The new and distinct variety of peach tree is of large size, vigorous, upright growth and a productive and regular bearer of large, firm, yellow flesh, semi-freestone fruit with excellent flavor and eating quality. The fruit is further characterized by holding firm on the tree 10 to 12 days after maturity (shipping ripe), having good handling and shipping quality, having a high degree of attractive red skin blush and having a mild, sweet, sub-acid taste. In comparison to the Sweet Gem Peach (U.S. Plant Pat. No. 7,952), which has a similar mild, sweet, sub-acid flavor, the fruit of the new variety is larger in size and is approximately one week later in maturity.

PHOTOGRAPH OF THE VARIETY

The accompanying color photographic illustration shows typical specimens of the foliage and fruit of the present new peach variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of peach tree, its flowers, foliage and fruit, as based on observations of specimens grown near Modesto, Calif., with color terminology (except those in common terms) in accordance with *Reinhold Color Atlas* by A. Kornerup and J. H. Wanscher.

Tree:

*Size.*—Large. Pruned to 12 to 14 feet in height and width at maturity for economical harvesting of fruit.

*Vigor.*—Vigorous. Developing 6 to 7 feet in height the first growing season. During the first dormant season the tree is pruned to 4 to 5 feet in height and primary scaffolds are selected for desirable tree growth.

*Form.*—Usually pruned to vase shape.

*Productivity.*—Productive. Fruit set varies from 1½ to several times more than needed for desirable tree cropload. Fruit is thinned and spaced to develop into desired market fruit size. Production varies with soil type, cultural practices and climatic conditions.

*Bearer.*—Regular. Varies with weather conditions at blooming time.

*Density.*—Medium dense. The tree is medium dense, usually pruned to a vase shape to allow air and sunlight to penetrate toward the center of tree to enhance fruit color and help off-set fungus and disease.

Trunk:

*Size.*—Large. Age of tree, 10 years. Circumference 19 inches, measured 10 inches above soil. Size of trunk may vary slightly with soil type, cultural practices, length of growing season and tree spacing.

*Texture.*—Medium shaggy.

*Color.*—Brown to soot brown (5-E-5) to (5-E-6).

Branches:

*Size.*—Medium. Pruned to 4 to 5 main scaffolds per tree. Scaffolds selected having proper angles and spacing in relationship to trunk. Lateral branches from scaffolds spaced to develop hangers for fruit wood and allow maximum sunlight to enhance fruit color and increase brix of fruit. Scaffold size taken 2 feet above ground level, average 11 inches in circumference. Measurements taken from 10 year old tree.

*Texture.*—Smooth to medium rough, varies with age of growth.

*Lenticels.*—Medium number, large size. The average number of lenticels varied from 32 to 38 on 4 square inch surface, approximately 30 inches from ground level on a 10 year old tree. The average size at that level is approximately 7/32 inch in length and 3/32 inch in width measured at the center of the lenticel. The lenticels decrease in size as the height from the ground increases and the branches become smaller.

*Color.*—Golden brown to brown (5-D-7) to (5-E-7), varies with age of growth.

Leaves:

*Size.*—Large. Average length 6¾ inches. Average width 1⅝ inches.

*Form.*—Lanceolate, printed.

*Margin.*—Crenate.

*Thickness.*—Medium.

*Surface.*—Smooth.

*Petiole.*—Medium length. Medium thickness.

*Glands.*—Number varies from 1 to 3. Average number 2. Reniform. Medium size. Located on upper portion of petiole and lower portion of leaf blade. Color — yellowish green to grayish green (30-C-8) to (30-D-8).

*Color.*—Upper surface — green to dark green (28-F-6) to (28-E-8). Lower surface — light green to green (28-E-4) to (28-E-6).

Flower buds:

*Size.*—Medium to large.

*Length.*—Medium.

*Form.*—Plump.

*Pubescence.*—Pubescent.

Flowers:

*Size.*—Large, showy. Average height 57/64 inch, measured from top of stigma to bottom of calyx. Average width 1 56/64 inches.

*Pollen.*—Present, self-fertile.

*Petal.*—Orbicular, slightly narrower at point of attachment. Edges vary from straight to slightly scalloped.

*Fragrance.*—Very slight.

*Blooming period.*—Date of first bloom: Mar. 5, 1996. Date of last bloom: Mar. 12, 1996. Varies slightly with climatic conditions.

*Color.*—Pink (12-A-2) to (12-A-3). Color fades as flowers get older.

Fruit:

*Maturity when described.*—Firm ripe.

*Date of first picking.*—Jun. 15, 1996.

*Date of last picking.*—Jun. 21, 1996. Varies slightly with climatic conditions.

*Size.*—Large. Average diameter axially 3 inches. Average transversely in suture plane 3¼ inches. Average weight 255 gram, varies from 227 to 267 grams. Weight of fruit varies slightly with amount of thinning, cultural practices and climatic conditions.

*Form.*—Nearly globose.

*Suture.*—Shallow, extends from base to apex.

*Ventral surface.*—Nearly smooth only slightly lipped.

*Apex.*—Slight apical point on most fruit.

*Base.*—Retuse.

*Cavity.*—Rounded to slightly elongated in suture plane. Average depth — ⅝ inch. Average breadth — 1 inch.

Stem:

*Length.*—Average length ⅜ inch. Average width ⅛ inch.

*Color.*—Varies from light green to spring green (30-C-6) to (30-C-8).

Flesh:

*Ripens.*—Relatively even, only slightly earlier near apex.

*Texture.*—Firm, meaty.

*Fibers.*—Few, small, tender.

*Aroma.*—Moderate. Sweet, sub-acid enhances flavor.

*Amygdalin.*—Undetected.

*Juice.*—Moderate.

*Eating quality.*—Excellent.

*Flavor.*—Excellent — mild, sweet, sub-acid.

*Color.*—Light yellow to yellow (4-A-4) to (4-A-6). Pit cavity — grayish yellow to yellowish gray (4-B-3) to (4-C-4).

*Brix.*—Average 12.1°. Varies slightly with number of fruit per tree, cultural practices and climatic conditions during maturity period.

Skin:

*Thickness.*—Medium, tenacious to flesh.

*Texture.*—Medium.

*Down.*—Moderate, medium length.

*Tendency to crack.*—None.

*Color.*—Yellow to golden yellow ground color (4-A-4) to (5-A-4). Overspread with light red to orange red (8-A-7) to (8-B-7).

Stone:

*Type.*—Semi-freestone.

*Size.*—Large. Average length 1½ inches. Average width 1 1/16 inches. Average thickness ¾ inch.

*Form.*—Varies from ovoid to obovoid.

*Base.*—Usually rounded, varies from straight to rounded.

*Apex.*—Acuminate.

*Surface.*—Irregularly furrowed toward apex, pitted toward base. Pits vary from round to elongated.

Ridges usually rounded. Longer furrows near edge of suture plane.

*Sides*.—Varies from unequal to equal.

*Tendency to split*.—None.

*Color*.—Light tan to light brown (6-C-6) to (6-D-6).

Use: Dessert. Market, local and long distance.

Keeping quality: Good, held firm in cold storage (38° to 42° F.) for three weeks without internal breakdown.

Shipping quality: Good. Packing and shipping trials revealed minimal bruising or scarring of flesh or skin.

Plant disease: No specific program of testing for disease resistance has been initiated. Under normal orchard practices and close observation by us, no excessive disease susceptibility has been observed.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of peach tree, substantially as illustrated and described, which is characterized by its large size, vigorous, upright growth; being a regular and productive bearer of large, yellow flesh, semi-freestone fruit with mild, sweet, sub-acid flavor and excellent eating quality; holds firm on the tree 10 to 12 days after maturity (shipping ripe); having good storage and shipping quality; and, in comparison to the sub-acid peach variety Sweet Gem (U.S. Plant Pat. No. 7,952), the new variety is approximately one week later in maturity.

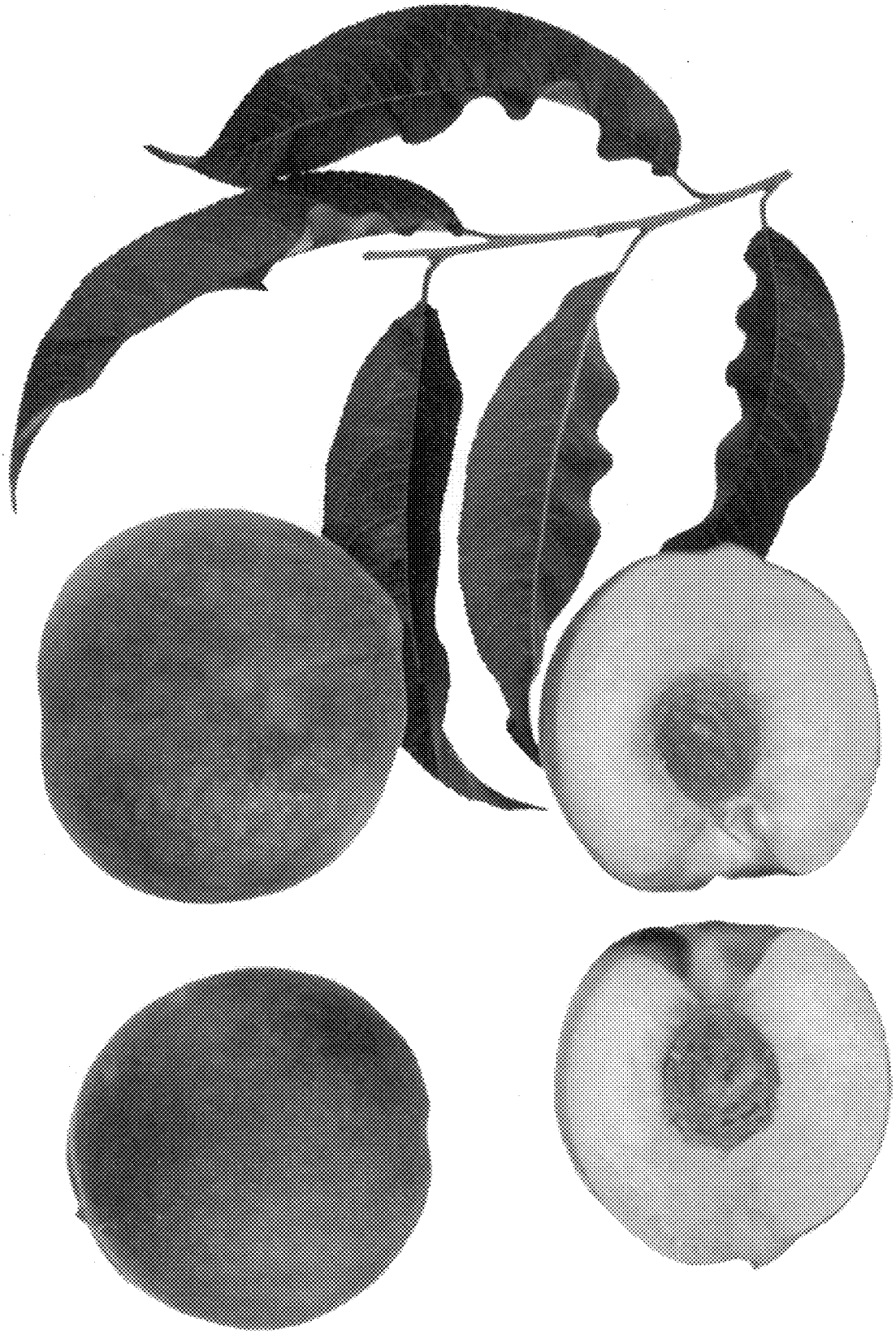

* * * * *